(12) United States Patent
Van Benthem et al.

(10) Patent No.: US 6,740,415 B2
(45) Date of Patent: *May 25, 2004

(54) POWDER PAINT BINDER COMPOSITION

(75) Inventors: Rudolfus A. T. M. Van Benthem, Sittard (NL); Saskia Udding-Louwrier, Zwolle (NL); Johan F. G. A. Jansen, Geleen (NL); Aylvin J. A. A. Dias, Maastricht (NL)

(73) Assignee: DSM N.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 09/754,243

(22) Filed: Jan. 5, 2001

(65) Prior Publication Data

US 2001/0007010 A1 Jul. 5, 2001

Related U.S. Application Data

(63) Continuation of application No. PCT/NL99/04408, filed on Jun. 30, 1999.

(30) Foreign Application Priority Data

Jul. 6, 1998 (EP) .............................. 98202239

(51) Int. Cl.$^7$ ........................ C09D 4/00; C09D 167/06; C08F 220/36; C08F 2/50; C07C 233/00
(52) U.S. Cl. ............................... 428/425.1; 428/435.8; 428/457; 428/458; 428/460; 428/474.4; 428/479.6; 428/480; 428/481; 428/511; 522/111; 522/137; 528/65; 528/288; 528/354; 528/367
(58) Field of Search ................. 522/152, 116, 522/117, 136, 137, 148, 149, 173, 90, 96, 100, 103, 104, 107, 111, 88, 89, 97; 428/425.1, 425.8, 457, 458, 460, 474.4, 479.6, 480, 481, 511; 528/65, 288, 354, 367

(56) References Cited

U.S. PATENT DOCUMENTS

| | | | |
|---|---|---|---|
| 3,366,613 A | | 1/1968 | Kelley |
| 3,928,499 A | * | 12/1975 | Tomalia et al. ............. 525/296 |
| 4,126,747 A | * | 11/1978 | Cowherd et al. ........... 544/388 |
| 4,209,581 A | * | 6/1980 | Takanashi et al. ........ 430/283.1 |
| 4,656,202 A | * | 4/1987 | Nason et al. ............. 428/425.1 |
| 4,665,123 A | * | 5/1987 | Goldenberg ................. 525/59 |
| 4,910,268 A | * | 3/1990 | Kobayashi |
| 4,912,239 A | * | 3/1990 | Bank et al. ................. 556/401 |
| 5,266,628 A | | 11/1993 | Essary et al. |
| 5,360,836 A | | 11/1994 | Chevallier et al. |
| 5,629,359 A | | 5/1997 | Peeters et al. |
| 6,245,829 B1 | * | 6/2001 | Meij et al. ................. 522/173 |
| 6,437,016 B2 | * | 8/2002 | Jansen et al. .............. 522/175 |
| 6,479,587 B1 | * | 11/2002 | Stockinger et al. ......... 525/131 |

FOREIGN PATENT DOCUMENTS

| | | | |
|---|---|---|---|
| EP | 0 263 749 A1 | * | 4/1988 |
| EP | 0525601 | | 2/1993 |
| JP | 03-336122 | | 11/1991 |
| JP | 5148429 | | 6/1993 |
| WO | WO9833855 | | 8/1998 |

* cited by examiner

*Primary Examiner*—Susan Berman
(74) *Attorney, Agent, or Firm*—Pillsbury Winthrop LLP

(57) ABSTRACT

The invention relates to a radiation curable powder paint binder composition comprising a radiation curable compound being a mono or multi valent carboxylic ester of a β, γ, δ, or ε-hydroxyalkylamide group containing compound, in which the carboxylic ester is derived from an α, β-ethylenically unsaturated carboxylic acid.

19 Claims, No Drawings

POWDER PAINT BINDER COMPOSITION

This is a continuation of: PCT/NL99/00408 filed Jun. 30, 1990 which designated the U.S., and that International Application was published under PCT Article 21(2) in English.

The invention relates to a powder paint binder composition.

As is evident from Powder Coatings Bulletin, 1996, 10, pp. 6–8, there is a market demand for radiation-curable powder paint formulations.

The object of the invention is to provide a radiation-curable binder composition that results in a powder coating with good properties, such as for instance a good storage stability and a viscosity at a relatively low curing temperature that is so low that a good flow can be obtained, and that also results in a powder paint formulation that can be cured on several substrates.

The invention is characterized in that the binder composition comprises a radiation curable compound, being a mono or multi valent carboxylic ester of a β, γ, δ or ε-hydroxyalkylamide group containing compound in which the carboxylic ester is derived from an α, β-ethylenically unsaturated caroxylic acid.

Preferably, the compound is an unsaturated amideester according to formula (I):

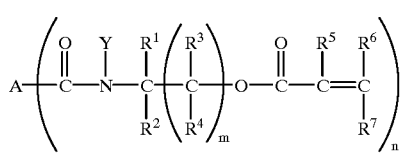

where:
A=hydrogen, or a monovalent or polyvalent organic group which is derived from a saturated or an unsaturated ($C_1$–$C_{60}$) alkyl group, or derived from an ($C_6$–$C_{10}$) aryl group or a polymer P,
Y=hydrogen, an ($C_1$–$C_8$) alkyl group or

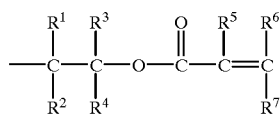

$R^1$, $R^2$, $R^3$, $R^4$ are, identical or different, hydrogen or a linear, branched or cyclic ($C_1$–$C_8$) alkyl chain,
$R^5$=hydrogen, ($C_1$–$C_5$)alkyl, —$CH_2OH$ or $CH_2COOX$,
$R^6$, $R^7$=hydrogen, ($C_1$–$C_8$) alkyl, ($C_6$–$C_{10}$)aryl or COOX,
X=hydrogen or ($C_1$–$C_8$) alkyl,
n=1–1000 and
m=1–4.

The organic groups in A may furthermore be substituted with, for example, ethers, esters, hydroxyl, amides, urethanes, acids, amines, urea or ketones.

$R^1$, $R^2$ or $R^3$ may form part of a cycloalkyl group.

Preferably, Y is hydrogen or methyl.
Preferably, $R^1$, $R^2$, $R^3$ and $R^4$ are hydrogen or methyl.
More preferably $R^1$, $R^2$, $R^3$ and $R^4$ are hydrogen.
$R^5$ is preferably hydrogen, (m)ethyl or $CH_2COOX$ or COOX.
$R^6$ and $R^7$ are preferably hydrogen or COOX.

Preferably n=1–100, more preferably n=1–20.
Preferably m=1–2, more preferably m=1.
Preferably, A is a monovalent organic group which is derived from a saturated ($C_1$–$C_{30}$) alkyl group.

According to another preferred embodiment of the invention A is a polyvalent organic group derived from a saturated ($C_2$–$C_{10}$) alkyl group or a $C_6$-aryl group.

Preferably A is substituted with urethanes or esters.

Suitable polymers P include, for example, addition polymers and condensation polymers. The polymers preferably have a molecular weight (Mw) of at least 400.

The polymers can be, for example, linear polymers, branched polymers, comb polymers, star polymers, ladder polymers, dendrimers and hyperbranched polymers.

Suitable addition polymers P include for example polymers derived from monomers such as (meth)acrylate, acrylamide, styrene, ethylene,propylene, maleic acid, cyanoacrylate, vinylacetate, vinylether, vinylchloride, vinylsilane and mixtures thereof.

Suitable condensation polymers P include, for example, polyesters, polylactones, polyamides, polyesteramides, polyethers, polyesterethers, polyurethanes and polyurethane-urea.

Suitable linear polymers P include, for example, polyethers derived from diols, polyethylene, polymethylmethacrylate, polyesters derived from diols and difunctional acids and/or mono-hydroxy acids.

Suitable branched polymers P include, for example, polyethers comprising at least one trifunctional alcohol unit, polyesters comprising at least one tri-or tetrafunctional alcohol unit and/or one tri/tetra-functional acid unit.

Suitable dendrimers are disclosed in for example EP-A-575596, EP-A-707611, EP-A-741756, EP-A-672703, Angew. Chem. Int. Ed. Eng. 1994, 33, 2413, Angew. Chem. Int Ed. Eng. 1990, 29, 138, Angew. Chem. Int. Ed. Eng. 1993, 32, 1308 and Angew. Chem. Int. Ed. Eng. 1992, 31, 1200.

Suitable hyperbranched polymers include, for example, condensation polymers containing β-hydroxyalkylamide groups and having a weight average molecular mass of ≧800 g/mol. The polymers can comprise at least two groups according to formula (III):

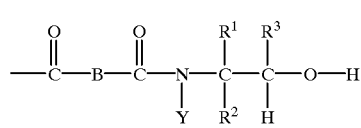

in which

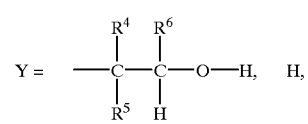

($C_1$–$C_{20}$)(cyclo)alkyl or ($C_6$–$C_{10}$) aryl,
B=($C_2$–$C_{20}$), optionally substituted, aryl or (cyclo)alkyl aliphatic diradical, and
$R^1$, $R^2$, $R^3$, $R^4$, $R^5$ and $R^6$ may, independently of one another, be the same or different, H, ($C_6$–$C_{10}$) aryl or ($C_1$–$C_8$)(cyclo)alkyl radical.

Other examples of suitable hyperbranched polymers are disclosed in WO-A-9612754, WO-A-9613558, WO-A-9619537 and WO-A-9317060.

Depending on the use it is also possible to use other functionalities besides the functional groups according to formula (I).

Between P and the functional group a connecting group S can be present:

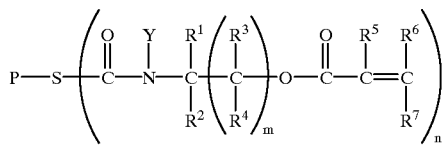

A suitable group S includes, for example, alkyl, oxyalkyl, urethanealkyl, ureaalkyl carboxyalkyl, aminoalkyl or amidoalkyl groups. The selected chain length of the groups depends on the use.

Generally, a binder composition comprises a polymer and a crosslinker. The unsaturated esteramide can be applied as the resin, as the crosslinker and as the complete powder paint binder composition. In these applications the softening point of the compound has to be higher than about 30° C. The compound can also be added to a composition comprising a polymer and a crosslinker.

In case the unsaturated esteramide functions as the crosslinker the binder composition further can comprise a binder polymer having generally an amount of polymerizable unsaturation—expressed as WPU—ranging from 145 to 3000 grams of polymer per mole of unsaturated group (WPU), and preferably from 300 to 2000 grams per mole of unsaturated group. The unsaturated groups may be positioned both within the chain and at the end of the chain.

The ratio polymer: crosslinker can be selected depending on the use of the powder paint.

Preferably, the binder polymer is an unsaturated polyester and/or an unsaturated polyacrylate. These polymers are, for example, disclosed in U.S. Pat. No. 5,703,198.

If this polymer is an unsaturated polyester, the amount of unsaturation is preferably between 300 and 1800 grams per mole of unsaturated group (WPU).

The molecular weight (Mn) generally ranges from 800 to 5000 and preferably from 2000 to 4500. Mn is determined by means of gel permeation chromatography (GPC) using a polystyrene standard.

The glass transition temperature (Tg) of an amorphous polyester generally lies between 25° C. and 100° C., and preferably between 30° C. and 80° C.

The melting point of a crystalline unsaturated polyester and of a crystalline crosslinker generally lies between 35° C. and 180° C., preferably between 50° C. and 120° C.

A general description of powder paint compositions containing unsaturated polyesters can be found in Powder Coatings, Chemistry and Technology, by Misev (Wiley; 1991) at pages 167–170.

In case the compound applied in the present invention functions as the binder polymer the powder paint binder composition further comprises a crosslinker.

The crosslinker can be amorphous or crystalline.

The glass transition temperature (Tg) of an amorphous crosslinker generally lies between 25° C. and 100° C., and preferably between 30° C. and 80° C.

The melting point of a crystalline crosslinker generally lies between 35° C. and 180° C., preferably between 50° C. and 120° C.

The number of polymerizable unsaturations of the crosslinker is higher than or equal to 2. This number is generally between 2 and 10, and is preferably 2–4.

The crosslinker can be either linear or branched. The WPU of the crosslinker generally ranges from 200 to 1500.

Preferably, the crosslinker comprises ethylenically unsaturated units, for example, vinyl ether, allylether, allylurethane, fumarate, maleate, itaconate or unsaturated acrylate units. Suitable unsaturated acrylates are, for example, unsaturated urethaneacrylates, unsaturated polyesteracrylates, unsaturated epoxyacrylates and unsaturated polyetheracrylates.

Suitable crosslinkers are, for example, crosslinkers, as disclosed in U.S. Pat. No. 5,703,198, having at least two functional groups consisting of vinyl ethers, vinyl ester or (meth)acrylate functional groups.

A suitable crosslinker is, for example, the reaction product of a hydroxyl-functional prepolymer, a (poly) isocyanate and a functional vinyl ether, an unsaturated alcohol, a hydroxy(meth)acrylate or an unsaturated amine.

The molecular weight (Mn) of the hydroxyl-functional prepolymer generally ranges from 200 to 2500.

The prepolymer for the crosslinker can be either saturated or unsaturated.

The hydroxyl-functional prepolymer can, for instance, be a polyester, polyacrylate, polyolefin, polyurethane or epoxy resin.

The hydroxyl number preferably ranges from 25 to 150.

Preferably use is made of saturated and/or unsaturated polyesters and/or polyacrylates.

Examples of suitable (poly)isocyanates are isophorone diisocyanate (IPDI), toluene diisocyanate, p- and m-phenylene diisocyanate, 1,4-tetramethylene diisocyanate, 1,6-hexamethylene diisocyanate (HDI), 2,2,4-trimethyl hexamethylene diisocyanate, 1,4-cyclohexane diisocyanate, 4,4'dicyclohexyl methane diisocyanate, 4,4,'-diphenylmethane diisocyanate, 1,5-tetrahydronaphthalene diisocyanate, naphthalene-1,5'-diisocyanate, 5-bis(2-methyl-3-isocyanate phenyl)methane, 4,4'-diphenylpropane diisocyanate tetramethyl xylene diisocyanate, 3,4-isocyanate methyl-1-methyl cyclohexyl isocyanate (IMCI), as well as higher functional isocyanate-functional-oligomers of these isocyanates such as, for instance, isocyanurates, uretdiones and biurets.

Preferably the isocyanate is IMCI, IPDI or HDI.

The vinyl ethers can for instance be a hydroxyvinyl ether or an aminovinyl ether.

Examples of suitable hydroxyvinyl ethers are hydroxyvinyl ethers with (2–10) C atoms. Preferably use is made of hydroxybutyl vinyl ether, hydroxyethyl vinyl ether, 4-hydroxymethyl cyclohexyl methyl vinyl ether, triethylene glycol monovinyl ether or diethylene glycol monovinyl ether.

An example of a suitable amino vinyl ether is aminopropyl vinyl ether.

Examples of suitable unsaturated alcohols are allyl alcohol and crotyl alcohol, which in the presence of a hydroxy polymer react with isocyanate to form an allyl- or crotyl-functionalized crosslinker. With the aid of, for instance, a rutene catalyst this crosslinker can then be converted into an alkenyl compound such as, for instance, 1-propenyl ether and 1-butenyl ether (Crivello, Pol. Mat. Sc. and Eng. 1995, Vol. 72, page 473).

Hydroxyvinyl ether and allyl alcohol are preferred.

Suitable hydroxy functional (meth)acrylates are, for example, hydroxy ($C_2$–$C_5$) (meth)acrylates.

According to a preferred embodiment of the invention the crosslinker comprises units of a prepolymer having a molecular weight higher than 400 and units of a vinyl ether or an unsaturated alcohol, the number of polymerisable unsaturation of the crosslinker being higher than or equal to 2.

The polymer and the crosslinker can be either (semi) crystalline or amorphous. Depending on the required application, a mixture of crystalline and amorphous compounds can be chosen in which the optimum balance of flow and processing properties can be obtained through the selection of the weight ratio.

It is also possible to use a combination of crosslinkers.

The compound applied in the present invention may also be applied as an additive to an UV-curable powder paint binder composition in an amount of, for example, 0,1–95 wt. % to improve properties, such as for example, adhesion, hardness, flexibility or flow. These powder paint binder formulations may further comprise unsaturated polyesters, unsaturated acrylates, vinyl functional polymers, vinyl ethers, allyl functional polymers, unsaturated polyester acrylates, unsaturated polyurethane acrylates, unsaturated polyether acrylates or unsaturated acrylated polyesters.

The radiation-curable system can contain a resin, a crosslinker, a photoinitiator, a flow agent and pigments.

Radiation curing of the binder composition according to the invention preferably takes place through UV and EB curing. These methods are described in more detail in, for instance, the article "UV and EB-curing" by S. J. Bett et al. in JOCCA 1990 (11), pp. 446–453.

The curing of the composition according to the invention use takes place via radical polymerization. Compared with cationic UV polymerization this method has the advantage that curing is not affected by moisture and proceeds completely almost at once (no dark reaction needed).

For the UV radiation curing of the powder paint formulation a photoinitiator can, at a temperature ranging from, for instance, 40° C. to 120° C., be mixed with a binder composition according to the invention.

Mixing can take place both in a solvent and in the melt, for instance in an extruder or in a static mixer.

Further, pigments and the desired auxiliary materials such as, for instance, flow agents can be added. The paint can subsequently be applied to the substrate or be sprayed electrostatically. After application, the powder paint is molten at temperatures ranging from, for instance, 40° C. to 170° C. by being placed in an oven, exposure to infra-red radiation, or a combination of both, so that a closed, smooth coating film is formed with a layer thickness ranging from, for instance, 20 to 200 µm, after which the still warm panel is cured under a UV light source. Afterwards post-heating may take place.

Examples of suitable photoinitiators are described in Volume 3 "Photoinitiators for free radical and cationic polymerisation" of "Chemistry and Technology of UV and EB formulations" by K. Dietliker (1991; SITA Technology Ltd., London).

Suitable photoinitiators allow for initiation of the curing process with exposure to light having wavelengths between about 200 nm and about 600 nm. Suitable photoinitiators have ketone functionalities and can be aromatic such as, for example, benzophenone. Darocur 1173® (Ciba) is a suitable benzyl-ketal-based photoinitiator, which contains 2-hydroxy-2-methyl-1-phenylpropane-1-one as an active component. Irgacure 184® (Ciba) is an aryl ketone containing hydroxycyclohexyl phenyl ketone as active component, and is a suitable photoinitiator. Irgacure 369® (active component 2-benzyl-2-dimethylaminol-1-(4-morpholinophenyl)-butanone-1) is also suitable. Acyl phosphines, such as for example 2,4,6,-trimethylbenzoyl diphenyl phosphone oxide (Lucerine TPO®, BASF) can also be used, as can Quantacure CPTX® (Octel Chemicals), which contains 1-chloro-4-propoxy thioxanthone as active component. Chemical derivatives of these photoinitiators are suitable, as are mixtures of these photoinitiators. A suitable combination of photoinitiators is Irgacure 1800™ (Ciba) consisting of 75% by weight Irgacure 184™ and 25% by weight (bis-(2,6-dimethoxy benzoyl)-2,4,4-trimethylpentyl phosphine oxide). Other suitable photoinitiators can be of the Norrish-II-type, for example, the combinations benzophenone with amine, maleimide with amine, thioxantone with amine and antrachinon with amine.

It has been found that the binder composition according to the invention can also yield a good coating after thermal curing under the influence of latent catalysts such as, for instance, peroxides. Thermal curing can take place at temperatures ranging from, for instance, 80° C. to 200° C., depending on the chosen polymers.

The powder paint compositions according to the invention can be applied to substrates as for example metal, plastic, wood, paper, cardboard and glass if the melting point of the binder system is low enough.

Examples of customary additives in the paint formulations are pigments, emulsifiers, preservatives, light stabilizers, UV absorption agents, flow agents, degassing agents, fillers, stabilizers and/or catalysts.

The invention will be further described based on the following non-limiting examples.

Experiment 1

Synthesis of ε-hydroxy -(N-ethyl-2-acryloyloxy) caproamide

To 12 grams of ε-hydroxy-pentyl oxazoline 18 grams of methacrylic acid were added slowly at 62° C., bubbling dry air through the liquid, while the reaction temperature raised to 90° C. After the addition the reaction mixture was stirred for 3 hours at this temperature. After cooling to room temperature the reaction mixture was poured into chloroform, washed thrice with a saturated sodium carbonate solution and once with a saturated sodium chloride solution. After evaporatin of the chloroform under reduced pressure ε-hydroxy -(N-ethyl-2-acryloyloxy) caproamide was obtained in approximately 81% yield.

Experiment 2

25 grams hydroxy functional amide ester methacrylate according to experiment 1 were dissolved in 60 ml toluene, together with 60,6 g of hydroxy polyester (Uralac ZW 3896 P of DSM Resins), 0,125 g N, N, N', N'-tetramethyl-1,6-hexane diamine, 0,006 g mono-tert-butylhydroquinon (MTBHQ) and 23 mg dibutyltin laurate (DBTL). To this solution were added 17,8 g hexanediisocyanate (HDI) in 40 ml toluene over a period of two hours at 80° C. Thirty minutes after the addition was finished 2,5 g n-butanol (n-BuOH) was added. One hour later the solvent and rest BuOH were removed by distillation and applying vacuum.

Experiment 3

21 g hydroxy functional amide ester methacrylate according to experiment 1 were dissolved in 25 ml toluene, together with 10 mg DBTL and 0.006 g MTBHQ. To this solution 7,5 g HDI were added in 25 ml toluene over a period of 1,5 hours at 80° C. Thirty minutes after the addition was finished 1,5 g n-BuOH was added. One hour later the solvent and rest n-BuOH were removed by distillation and applying vacuum.

Experiment 4

398 g of hexahydrophthalic anhydride and 408 g of diisopropanolamine were introduced into a double-walled glass reactor, which could be heated by means of thermal oil, fitted with a mechanical stirrer, a distillation head and nitrogen and vacuum connections. The reaction mixture was gradually heated, with stirring, to 70° C. and then more slowly to 160° C. A vacuum was created during the heating. The pressure in the reactor was adjusted to the release of reaction water, so that this could be removed from the reactor by means of distillation. After a total reaction time of 3.5 hours the viscous polymer contained less than 0.2 meq/g of carboxylic acid (titrimetrically determined) and no more water could be removed through distillation. After cooling the polymer was obtained as an almost colourless glassy mass. The concentration of hydroxyl groups was titrimetrically found to be 5.2 meq/g.

190 g of the obtained hydroxyfunctional polyesteramide was heated to 100° C. in the same reactor. Next 100 ml xylene, 22 g methacrylic acid and 50 mg fenothiazine were added. The temperature was raised to 140° C. and after 8 hours destillation with a Dean Stark unit 4,5 ml water were obtained. After cooling and drying under vacuum the resulting polymer was a slightly brown coloured glassy mass.

Experiment 5

208 g of hexahydrophthalic anhydride, 108 g of benzoic acid and 436 g of diisopropanolamine were introduced into a double-walled glass reactor, which could be heated by means of thermal oil, fitted with a mechanical stirrer, a distillation head and nitrogen and vacuum connections. The reaction mixture was gradually heated, with stirring, to 70° C. and then more slowly to 160° C. A vacuum was created during the heating. The pressure in the reactor was adjusted to the release of reaction water, so that this could be removed from the reactor through distillation. After a total reaction time of 4,5 hours the viscous polymer contained less than 0.05 meq/g carboxylic acid (titrimetrically determined) and no more water could be removed through distillation. After cooling the polymer was obtained as an almost colourless glassy mass. The concentration of hydroxyl groups was titrimetrically found to be 2.8 meq/g.

The obtained hydroxyfunctional polyesteramide was heated to 100° C. in the same reactor. Next 200 ml xylene, 60 g methacrylic acid and 200 mg fenothiazine were added. The temperature was raised to 140° C. and after 8 hours destination with a Dean Stark unit 1,5 ml water were obtained. After cooling and drying under vacuum the resulting polymer was a slightly brown coloured glassy mass.

Experiment 6

Under a flow of nitrogen, 200 g of hydroxy polyester (Uralac ZW 3896 P) were dissolved in 300 g of toluene at 100° C. Then, 39.5 g hydroxyethylacrylate, 0.3 g MTBHQ, 0.30 g N, N, N', N'-tetramethyl-1,6-hexane diamine and 0.03 g DBTL were added. The solution was cooled to 70° C., and 58.7 g of hexamethylene diisocyanate was added in 2.5 hours. Thirty minutes after the addition was finished, the toluene was removed by vacuum distillation at 125° C. to yield solid urethane acrylate.

EXAMPLE I 50 g of amide estermethacrylate according to experiment 2, 50 of unsaturated polyester (Uralac XP3125 P of DSM Resins), 1 g of Irgacure 184™ and 1 g of Resiflow PV 5 were homogeneously mixed in a prism extruder at 70° C. and 200 rpm. After cooling, the paint was ground and sieved, the fraction having a particle size lower than 90 μm being applied, in a layer thickness of about 100 μm, on an aluminium panel by means of electrostatic spraying device. The resulting powder coating was heated at 120° C. for 60 seconds by means of IR lamps, so that the powder layer melted. The panel, which was still warm, was cured by means of UV-radiation (1 J/cm², measured using an IL 390 light bug, Standard Mercury arc lamp). The resulting coating had a good flow (visually determined), a good acetone resistance, an impact resistance of 60 inch pound, a good adhesion (Gitterschnitt 0) and an ESP of 6.0 mm.

EXAMPLE II

With 25 g of amide estermethacrylate according to experiment 3, 75 g of unsaturated polyester (Uralac P3125 P of DSM Resins), 1 g of Irgacure 184™ and 1 g of Resiflow PV 5 a coating was prepared according to the method described in Example I. The resulting coating had a good flow (visually determined) and a good acetone resistance.

EXAMPLE III

With 100 g of amide estermethacrylate according to experiment 4, 1 g of flow additive BYK 361™ an 1 g of Irgacure 184™, a coating was prepared according to the method described in Example I. The coating had a good flow (visually determined) and a good acetone resistance.

EXAMPLE IV

With 100 g of amide estermethacrylate according to experiment 5, 1 g of flow additive BYK 361™ and 1 g of Irgacure 184™, a coating was prepared according to the method described in Example I. The coating had a good flow (visually determined) and a good acetone resistance.

EXAMPLE V

With 50 g of amide estermethacrylate according to experiment 4, 41,5 g of unsaturatued polyester (Uralac XP3125 P of DSM Resins), 8.5 g of vinyl ether crosslinker (Uralac ZW3307 P of DSM Resins), 1 g of flow additive BYK 361™ and 1 g of Irgacure 184™, a coating was prepared according to the method described in Example I. The coating had a good flow (visually determined) and a good acetone resistance.

EXAMPLE VI

With 50 g of amide estermethacrylate according to experiment 4, 18 g of polyester (Uralac XP3125 P), 32 g of urethane acrylate according to experiment 6, 1 g of flow additive BYK 361™ and 1 g of Irgacure 184™, a coating was prepared according to the method described in Example I. The coating had a good flow (visually determined) and a good acetone resistance.

What is claimed is:

1. A radiation curable compound represented by the following formula (I) and which is a mono or multi valent carboxylic acid ester of a β, γ, δ or ε-hydroxy-alkylamide group containing compound, wherein the ester is derived from an α, β-ethylenically unsaturated carboxylic acid:

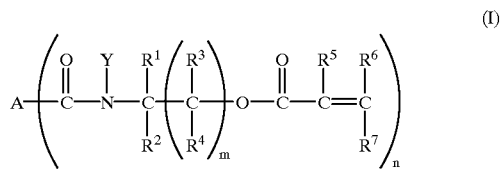

(I)

where:
A=a condensation polymer P which is a polyester, polylactorie, polyamide, polyesteramide, polyesterether, polyurethane, polyurethane-urea, a linear polyether derived from diol, or branched polyether comprising at least one trifunctional alcohol unit;
Y=hydrogen, an alkyl group having from 1 to 8 carbon atoms or

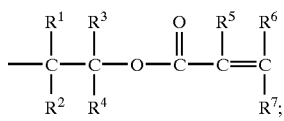

$R^1$, $R^2$, $R^3$, $R^4$ are, identical or different, hydrogen or a linear, branched or cyclic ($C_1$–$C_8$) alkyl chain;
$R^5$=hydrogen, ($C_1$–$C_5$) alkyl, —$CH_2OH$ or $CH_2COOX$;
$R^6$, $R^7$=hydrogen, ($C_1$–$C_8$) alkyl, ($C_6$–$C_{10}$) aryl or COOX;
X=hydrogen or ($C_1$–$C_8$) alkyl;
n=1–1000 and
m=1–4.

2. The radiation curable compound according to claim 1, wherein said condensation polymer P is a hyperbranched polymer.

3. The radiation curable compound according to claim 2, wherein said condensation polymer P is a hyperbranched polymer containing β-hydroxyalkylamide groups and having a weight average molecular mass of at least 800 g/mol.

4. The radiation curable compound according to claim 2, wherein said condensation polymer P is a hyperbranched polymer comprising at least two groups according to formula (III):

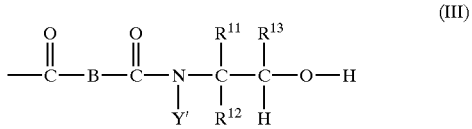

in which

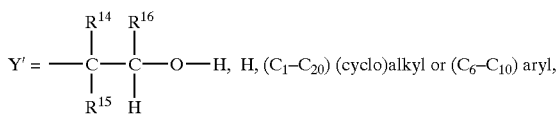

B=($C_2$–$C_{20}$), optionally substituted, aryl or (cyclo)alkyl aliphatic diradical, and
$R^{11}$, $R^{13}$, $R^{14}$, $R^{15}$ and $R^{16}$, which may be the same or different, represent, H, ($C_6$–$C_{10}$) aryl or ($C_1$–$C_8$)(cyclo) alkyl radical.

5. The radiation curable compound according to claim 1, wherein A represents polyesteramide.

6. Radiation curable compound according to claim 1, wherein Y is hydrogen or methyl and $R^1$, $R^2$, $R^3$, and $R^4$ are hydrogen or methyl.

7. Composition comprising a radiation curable compound according to claim 1, further comprising a polymer having an amount of polymerizable unsaturation ranging from 145 to 3000 grams of polymer per mole of unsaturated group (WPU).

8. Composition comprising a radiation curable compound according to claim 1, further comprising a crosslinker for the radiation curable compound.

9. A film obtained by radiation curing the composition of claim 7.

10. A substrate of which at least a portion is coated with a coating obtained by radiation curing the composition of claim 7.

11. Powder paint composition comprising a radiation curable compound according to claim 1, further comprising at least one powder paint additive.

12. Powder paint composition comprising a binder composition comprising a radiation curable compound according to claim 1 and at least one polymer having an amount of polymerizable unsaturation ranging from 145 to 3000 grams of polymer per mole of unsaturated group (WPU).

13. Powder paint composition comprising a binder composition comprising a radiation curable compound according to claim 1 and at least one polymer, wherein the polymer comprises unsaturated polyester or unsaturated polyacrylate or mixture thereof.

14. Powder paint composition comprising a binder composition comprising a radiation curable compound according to claim 1 and at least one crosslinker for the radiation curable compound.

15. Powder paint composition according to claim 14, wherein the crosslinker comprises units of a prepolymer having a molecular weight higher than 400 and units of a vinyl ether or an unsaturated alcohol, the number of polymerizable unsaturation of the crosslinker being 2 or higher.

16. Powder paint composition according to claim 11, wherein the powder paint additive comprises at least a photoinitiator.

17. A film obtained by radiation curing the powder paint composition of claim 11.

18. A substrate of which at least a portion is coated with a coating obtained by radiation curing the powder paint composition according to claim 11.

19. A substrate according to claim 18, in which the substrate is metal or wood.

* * * * *

UNITED STATES PATENT AND TRADEMARK OFFICE
CERTIFICATE OF CORRECTION

PATENT NO.    : 6,740,415 B1
DATED         : May 25, 2004
INVENTOR(S)   : Van Benthem et al.

It is certified that error appears in the above-identified patent and that said Letters Patent is hereby corrected as shown below:

Title page,
Item [*] Notice, please delete the following statement: "This patent is subject to a terminal disclaimer."

Signed and Sealed this

Sixteenth Day of November, 2004

JON W. DUDAS
*Director of the United States Patent and Trademark Office*